United States Patent [19]
Bakke

[11] Patent Number: 5,420,962
[45] Date of Patent: May 30, 1995

[54] CONVECTION BLOOD WARMING SYSTEM WITH DISPOSABLE FLATTENED TUBE ENVELOPE HAVING VENT INCORPORATING A HYDROPHOBIC FILTER

[76] Inventor: Allan P. Bakke, 609 19th Ave., SW., Rochester, Minn. 55902

[21] Appl. No.: 140,487

[22] Filed: Oct. 25, 1993

[51] Int. Cl.⁶ .......................... A61F 7/00; F24H 1/20
[52] U.S. Cl. .................... 392/470; 392/379; 392/480; 604/114; 604/405; 604/408
[58] Field of Search ............... 392/470, 379, 468, 480; 604/114, 113, 408, 405, 403; 128/911, 203.27, 203.26, 201.13, 204.17; 607/106; 96/218, 219; 95/251, 252

[56] References Cited

U.S. PATENT DOCUMENTS

| | | | |
|---|---|---|---|
| 1,995,302 | 3/1935 | Goldstein | 392/470 |
| 3,590,215 | 6/1971 | Anderson et al. | 392/470 |
| 4,132,594 | 1/1979 | Bank et al. | 604/405 |
| 4,294,594 | 10/1981 | Sloane, Jr. et al. | 55/186 |
| 4,356,012 | 10/1982 | Hofstetter | 604/405 |
| 4,392,858 | 7/1983 | George et al. | 604/187 |
| 4,515,606 | 5/1985 | de Winter | 55/178 |
| 4,534,757 | 8/1985 | Geller | 604/126 |
| 4,707,587 | 11/1987 | Greenblatt | 392/470 |
| 4,734,269 | 3/1988 | Clarke et al. | 96/219 |
| 4,795,457 | 1/1989 | Cooney | 604/408 |
| 5,013,889 | 5/1991 | Bakke | 392/470 |
| 5,106,373 | 4/1992 | Augustine et al. | 604/113 |
| 5,297,234 | 3/1994 | Harms et al. | 392/470 |

FOREIGN PATENT DOCUMENTS

| | | | |
|---|---|---|---|
| 2035584 | 2/1991 | Canada . | |
| 2331230 | 6/1977 | France | 392/470 |
| 2403082 | 4/1979 | France | 392/470 |

OTHER PUBLICATIONS

"Hotline & System 250" Brochure, Level 1 Technologies Inc., 160 Weymouth St., Rockland Mass. 02370, 1992.

*Primary Examiner*—John A. Jeffery
*Attorney, Agent, or Firm*—L. Paul Burd; Richard O. Bartz; Robert W. Gutenkauf

[57] ABSTRACT

A system for warming blood or other liquids to body temperature for infusion into a patient. The system includes a blood warmer apparatus having a pair of closely spaced apart heat transfer plates, each of which forms one face of a housing containing flat vapor condensation heating units. A flat disposable heat exchanging blood warming envelope is held clamped between the heat transfer plates. The envelope is provided with an air escape vent covered by a hydrophobic filter eliminating the need for a vent separate check valve. An air heating unit in one of the apparatus housings includes a cool air inlet, heat transfer fins on the walls of the vapor condensation heater unit, a fan and guides for conducting air past those fins and a warmed air outlet. An external elongated insulated air hose is connected at one end to the warmed air outlet and extends to the patient. The blood flow line from the outlet of the heat exchanging envelope is positioned within the warmed air hose to maintain the physiologic temperature of the blood.

19 Claims, 6 Drawing Sheets

CONVECTION BLOOD WARMING SYSTEM WITH DISPOSABLE FLATTENED TUBE ENVELOPE HAVING VENT INCORPORATING A HYDROPHOBIC FILTER

BACKGROUND OF THE INVENTION

1. Field of the Invention

This invention relates to a system for warming blood and other liquids to physiologic temperature before infusion into a patient. The system is characterized by disposable heat exchanging blood warming envelopes with automatic gas bubble venting and to the provision of active warm air insulation of the intravenous line to the patient.

Blood is stored at approximately 4 degrees C. prior to transfusion and should be warmed to physiologic temperature of about 35 to 40 degrees C. for transfusion. Infusion of cold fluids at high flow rates can cause cardiac arrhythmia, cardiac arrest and death. Even at low flow rates it is desirable to warm intravenous liquids for delivery to the patient, especially if the patient is an infant or child.

In the intravenous administration of blood products and other intravenous liquids, it is necessary that the liquid being administered to the patient be free of entrained air or other gas bubbles to prevent venous gas embolism and its potentially fatal consequences. The present system is designed to deliver warmed liquids from very low flow rates to high flow rates of 500 ml/min. or more. At high flow rates significant volumes of gas bubbles are generated during the warming process. These must be removed before administration of the liquid to the patient.

2. The Prior Art

My prior U.S. Pat. No. 5,013,889 is directed to an electric blood warmer utilizing heating by vapor condensation. The disclosure of that patent is incorporated herein by references.

One commercially available blood warmer which can maintain physiologic temperature to the patient connection is that designated "Hotline" from Level 1 Technologies of Rockland, Mass. This unit, however, can provide flow rates of only 50 ml/min. Level 1 System 250 is a high flow rate blood warmer but utilizes patient intravenous flow lines exposed to room air and at low flow rates delivers liquid to the patient connection at temperatures substantially below physiologic temperature. In that system a hydrophobic film gas vent and filter in the patient flow line is utilized. To prevent air from entering the patient line through the hydrophobic gas vent in the event of sub-atmospheric pressure in the line, a separate check valve element must be incorporated. One object of the present invention is to provide a simplified and economical automatic gas bubble vent incorporated into the plastic heat exchanging envelope, thus eliminating the separate check valve.

George et al U.S. Pat. No. 4,392,858 issued Jul. 12, 1983 discloses a wound drainage device optionally including a gas or air vent covered by a hydrophobic sheet filter.

Sloane et al U.S. Pat. No. 4,294,594 issued Oct. 13, 1981 discloses a filter assembly for removing particulate material, bacteria and air from an intravenous solution which includes hydrophobic filters.

Geller U.S. Pat. No. 4,534,757 issued Aug. 13, 1985 discloses a device for introducing active ingredients into a liquid flow parenteral administration system which includes a receptacle through which the liquid flows having preferably hydrophobic filters.

Greenblatt U.S. Pat. No. 4,707,587 issued Nov. 17, 1987 discloses a blood warming apparatus using a gaseous heat exchange medium.

SUMMARY OF THE INVENTION

Broadly stated the present invention is directed to a system for warming blood or other liquids to body temperature for infusion into a patient. The system includes a blood warmer apparatus having a pair of closely spaced apart heat transfer plates, each of which forms one face of a housing containing flat vapor condensation heating units therein. A flat disposable heat exchanging blood warming envelope is held clamped between the spaced apart heat transfer plates. That envelope has a blood inlet adapted to be connected to a source of blood to be warmed and a blood outlet adapted to be connected to a flow line to the patient. The envelope additionally is provided with an air escape vent adjacent to its topmost edge and a hydrophobic filter covering that vent. An air heating unit in one of the apparatus housings includes a cool air inlet, heat transfer fins on the walls of the vapor condensation heater unit opposite from the heat transfer plate, a fan and guides for conducting air past those fins and a warmed air outlet from the housing. An external elongated air hose is connected at one end to the warmed air outlet and extends to the patient, The blood flow line from the warmed blood outlet of the heat exchanging envelope is positioned within the warmed air hose, The air hose is insulated to maintain the physiologic temperature of the blood.

BRIEF DESCRIPTION OF THE DRAWINGS

The invention is illustrated by the accompanying drawings in which corresponding parts are identified by the same numerals and in which.

DETAILED DESCRIPTION OF THE PREFERRED EMBODIMENTS

Figure 1:
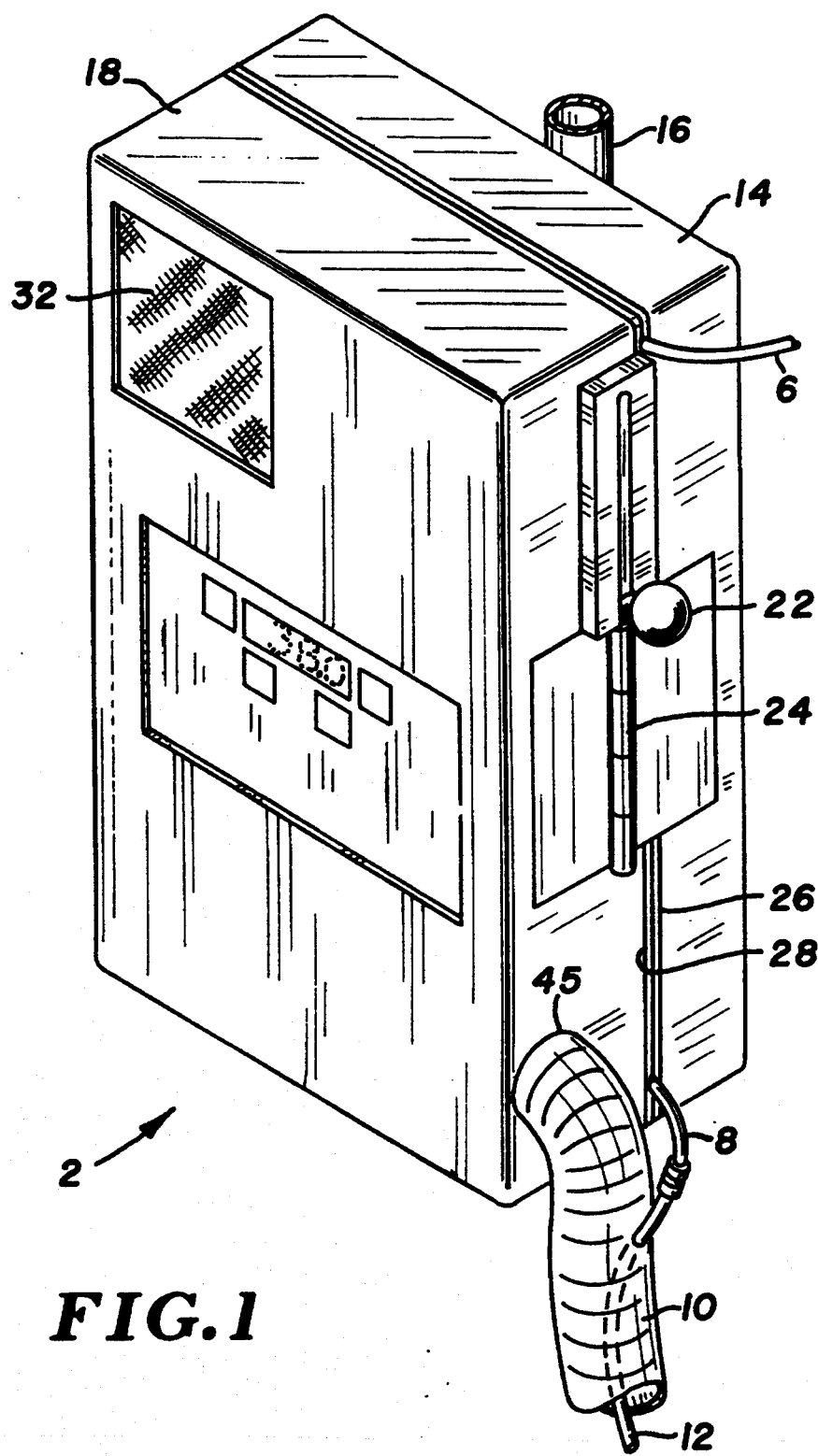
FIG. 1 is an isometric view of the blood warming system according to the present invention incorporating an electric blood warmer utilizing heating by condensation.
Figure 2:
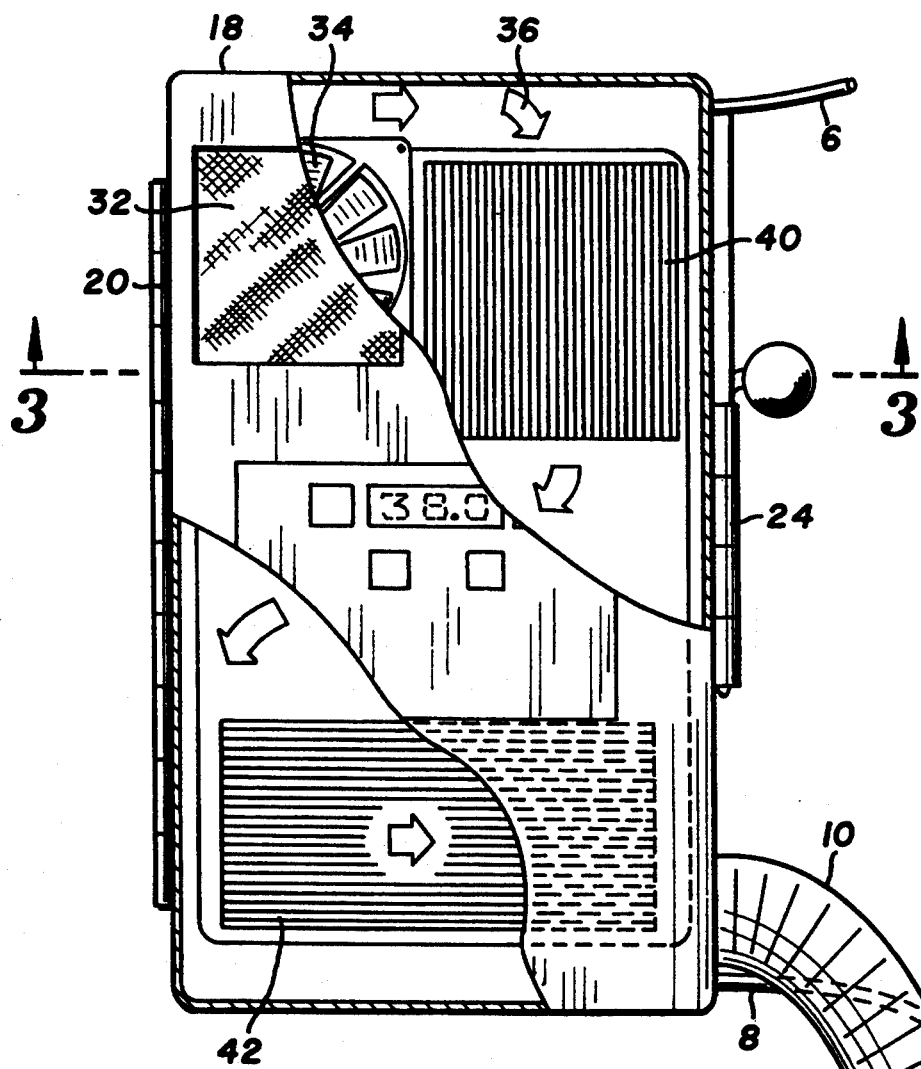
FIG. 2 is a front elevational view of the blood warmer apparatus with its outer housing partially broken away.
Figure 3:
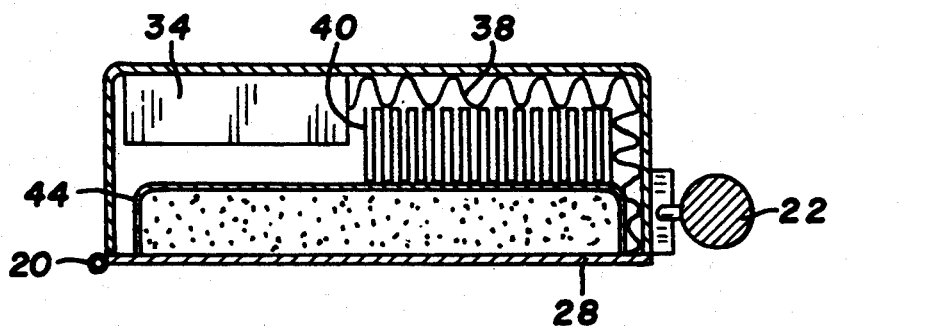
FIG. 3 is a horizontal cross section through one housing unit on the line 3—3 of FIG. 2 and in the direction of the arrows.
Figure 4:
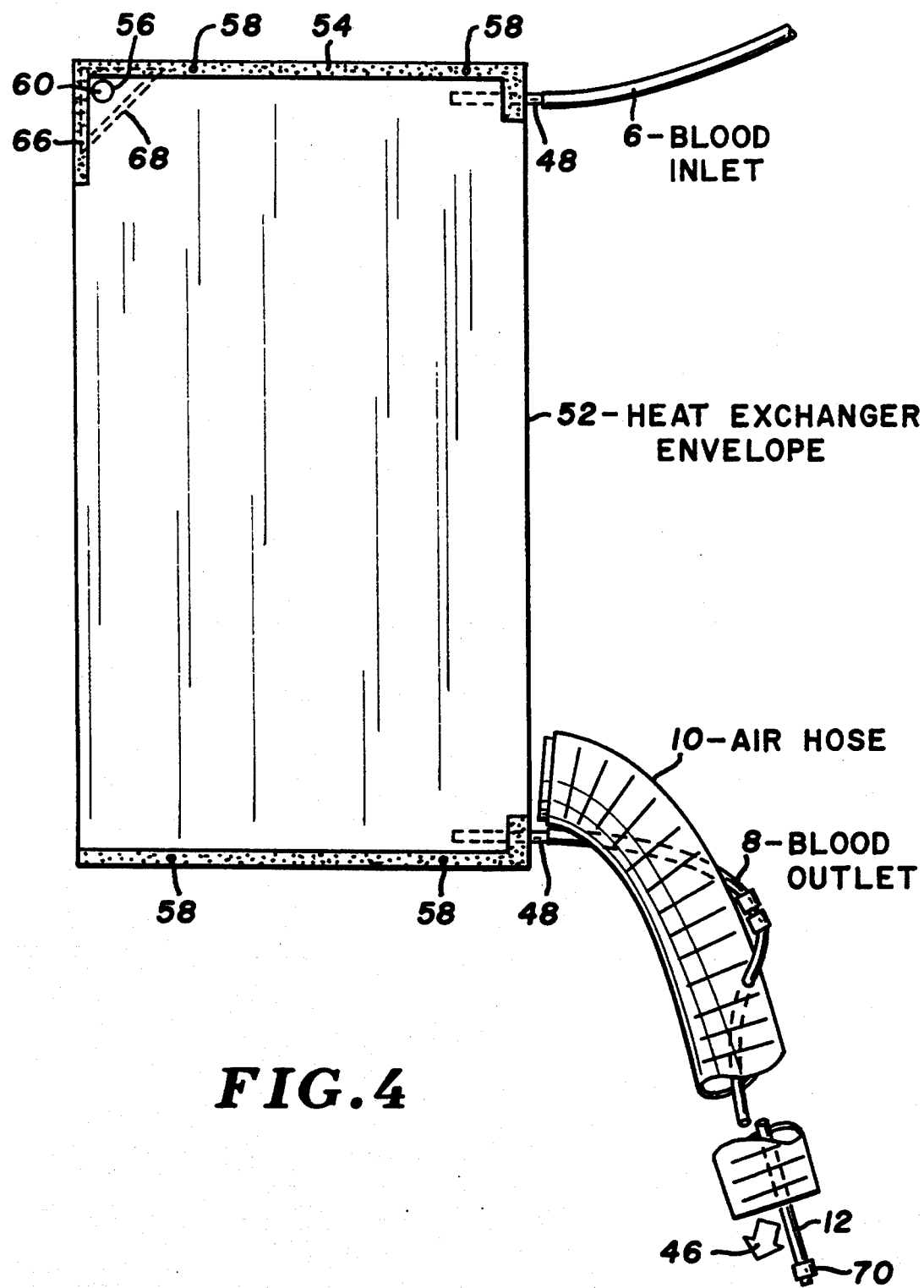
FIG. 4 is a front elevational view of one embodiment of a disposable heat exchanging blood warming envelope showing one manner of use of the warm air hose.

Referring now to the drawings, and particularly to FIGS. 1 through 3, there is shown an electric blood warmer apparatus utilizing heat by condensation indicated generally at 2 and including a pair of housing units 14 and 18. Fixed housing unit 14 is removably mounted on the pole or standard 16 of a conventional intravenous stand. A movable housing unit 18 is hinged at 20 to fixed housing unit 14 to permit the housing to be opened for insertion of a disposable heat exchanging blood warming plastic envelope 52, as hereinafter described in detail. As described in my prior U.S. Pat. No. 5,013,889, the inside face of each housing unit comprises a heat transfer plate 26 and 28, respectively, and comprises one wall of a flat vapor condensation heating unit as described in the patent. When the movable housing unit 18 is in closed position a reciprocable latch pin 22 engages a latch 24 to hold heating plates 26 and 28 closely spaced apart and parallel to each other.

A plurality of parallel closely spaced apart heat transfer fins 40 and 42 of heat conducting metal are brazed or otherwise bonded to isothermal surface 44 of the vapor condensation heating unit within housing unit 18. A screened air inlet 32 in the wall of housing unit 18 permits air to be drawn into the housing by fan 34 while filtering out dust or other particulate material in the air. Arrows 36 show generally the course of air flow inside housing unit 18 directed by baffles 38 of flexible insulating material to pass over the heat transfer fins to a warmed air outlet 45 connected to warm air hose 10. Arrow 46 shows the path of warmed air inside the warm air hose. As described hereinafter, the hose 10 maintains the physiologic temperature of the warmed blood in its passage between the blood warmer and the patient to be transfused. Hose 10 is flexible and preferably made of a lightweight insulating material such as closed cell polyethylene foam.

Referring now to FIGS. 4, 5, 7 and 9 there is shown an automatically gas bubble venting disposable heat exchanging blood warming envelope 52 for use with the blood warming apparatus 2. Envelope 52 is of a size to fit between the heat transfer plates 26 and 28 of the warmer apparatus. The envelope 52 is formed from thin flexible heat sealable synthetic resinous plastic sheet material such as 4 mil flat-lay polyethylene tubing. The end openings of the flat plastic tube are heat sealed at 54 to form top and bottom end edges. Mounting holes 58 are provided through the top and bottom end seals 54 located to engage similarly located pins 74 on one of the heat transfer plates 26 or 28 to prevent incorrect installation of the heat exchanging envelope.

A relatively short inlet/outlet tube 48, preferably polyethylene, is collar heat sealed between the two faces of the heat exchanging envelope closely adjacent to the top and bottom end edges of the envelope projecting outwardly from the same side edge of the envelope and extending a short distance within the envelope. Tubes 48 have an inside diameter of about $\frac{1}{8}$ to $\frac{1}{4}$ inch. A flexible blood inlet tube 6 is press fit over one of said inlet/outlet tubes 48 at one end of the envelope and a similar blood outlet tube 8 is connected to the other tube 48 at the opposite end of the envelope. Tubes 48 are interchangeable as inlets or outlets depending upon whether the blood to be warmed flows upwardly or downwardly through the blood warmer. In the embodiment shown in FIG. 4 the cold blood enters at the top of the envelope and the warmed blood exits from the bottom. In the embodiment shown in FIG. 5 the cold blood enters at the bottom of the envelope and flows upwardly to be discharged from the top. In both instances the blood outlet tube 8 is connected to tubing 12 which penetrates the wall of warm air hose 10 adjacent to the warm air outlet from the housing 18 and passes through hose 10 to the patient connection 70.

An air discharge port or vent 56 is provided in one of the side walls of envelope 52 adjacent the top edge and adjacent the side edge opposite from inlet/outlet tube 48. Air exit vent 56 is covered by a hydrophobic filter which prevents the passage of liquid while permitting the passage of air and other gases. For example, a right triangular patch of commercially available hydrophobic film 60 is heat sealed along its hypotenuse 68 to the inside surface of the envelope wall containing the air vent 56. The hydrophobic film is then sealed at 66 between the two walls of the heat exchanging envelope along the triangle's other two sides. Other configurations may be used.

The hydrophobic film vent automatically removes gas bubbles by allowing gas to flow from inside the heat exchanging envelope to the atmosphere while preventing the passage of blood. In the occurrence of sub-atmospheric pressure inside the envelope near the hydrophobic film vent, external atmospheric pressure causes the two faces of the envelope to collapse together, acting as a check valve and preventing entrance of air through the vent. This permits the elimination of the separate check valve present in some systems.

Commercially available hydrophobic filter materials include "Gore-Tex" sold by W. L. Gore & Associates, "Tyvek" sold by duPont and "Acropor" sold by Gelman Instrument Company of Ann Arbor, Mich.

Figure 7:
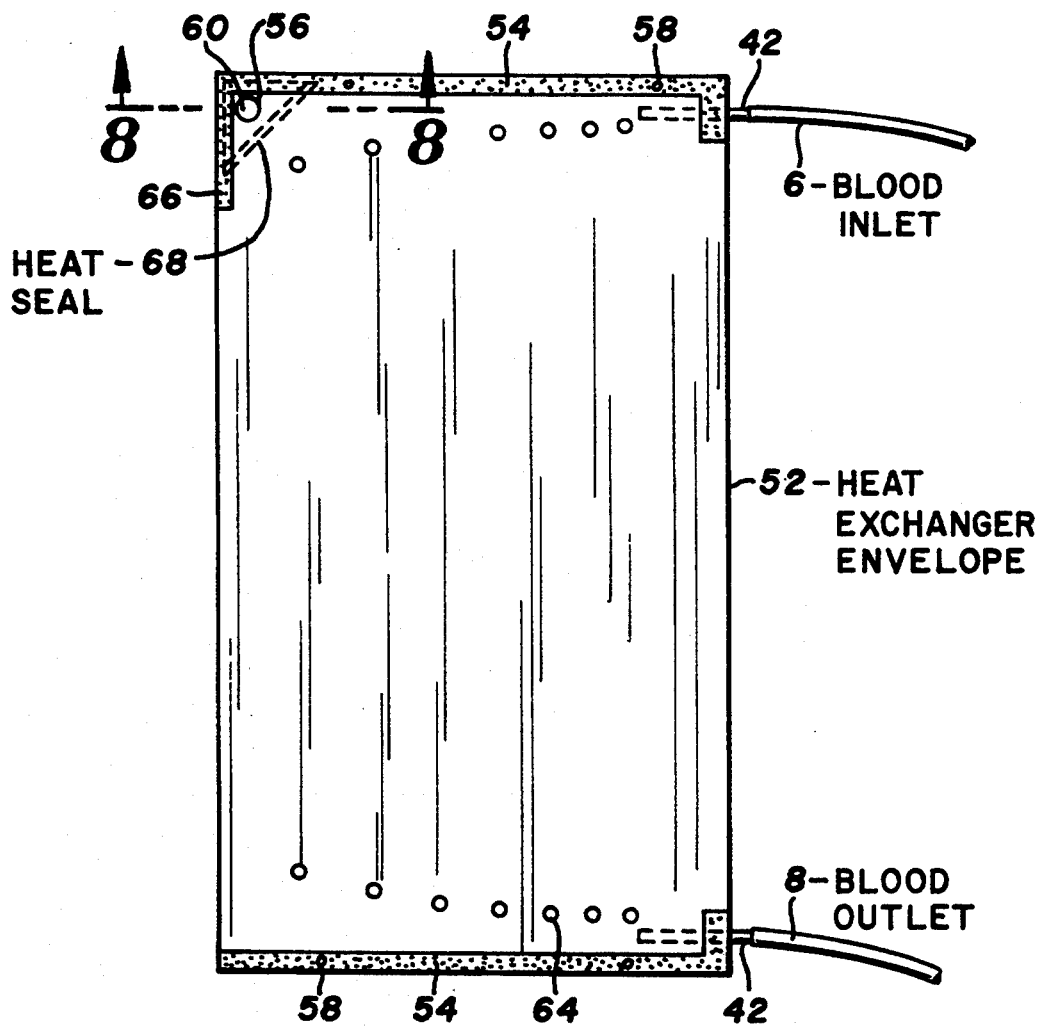
FIG. 7 is a front elevational view of a modified form of disposable heat exchanging blood warming envelope.
Figure 8:
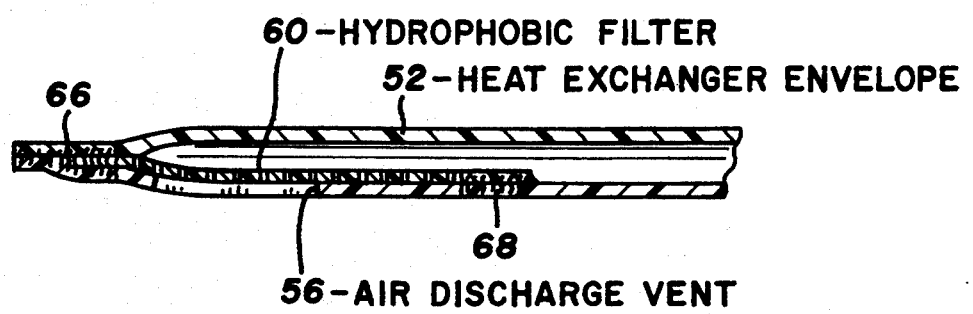
FIG. 8 is a horizontal section on an enlarged scale on line 8—8 of FIG. 7 and in the direction of the arrows.

As shown in FIG. 7, the heat exchanging envelope 52 is desirably provided with a plurality of flow distributing channels formed by spaced apart heat seal spots 64 between the opposite side walls of the envelope. These flow distributing channels are provided in both the inlet and outlet regions to facilitate uniform fluid flow distribution across the full width of the envelope. The sealed spots are more closely spaced near the inlet and outlet edge of the envelope and slope slightly toward the opposite side edge and away from the top and bottom edges to direct some of the flow preferentially away from the inlet edge of the envelope.

Figure 5:
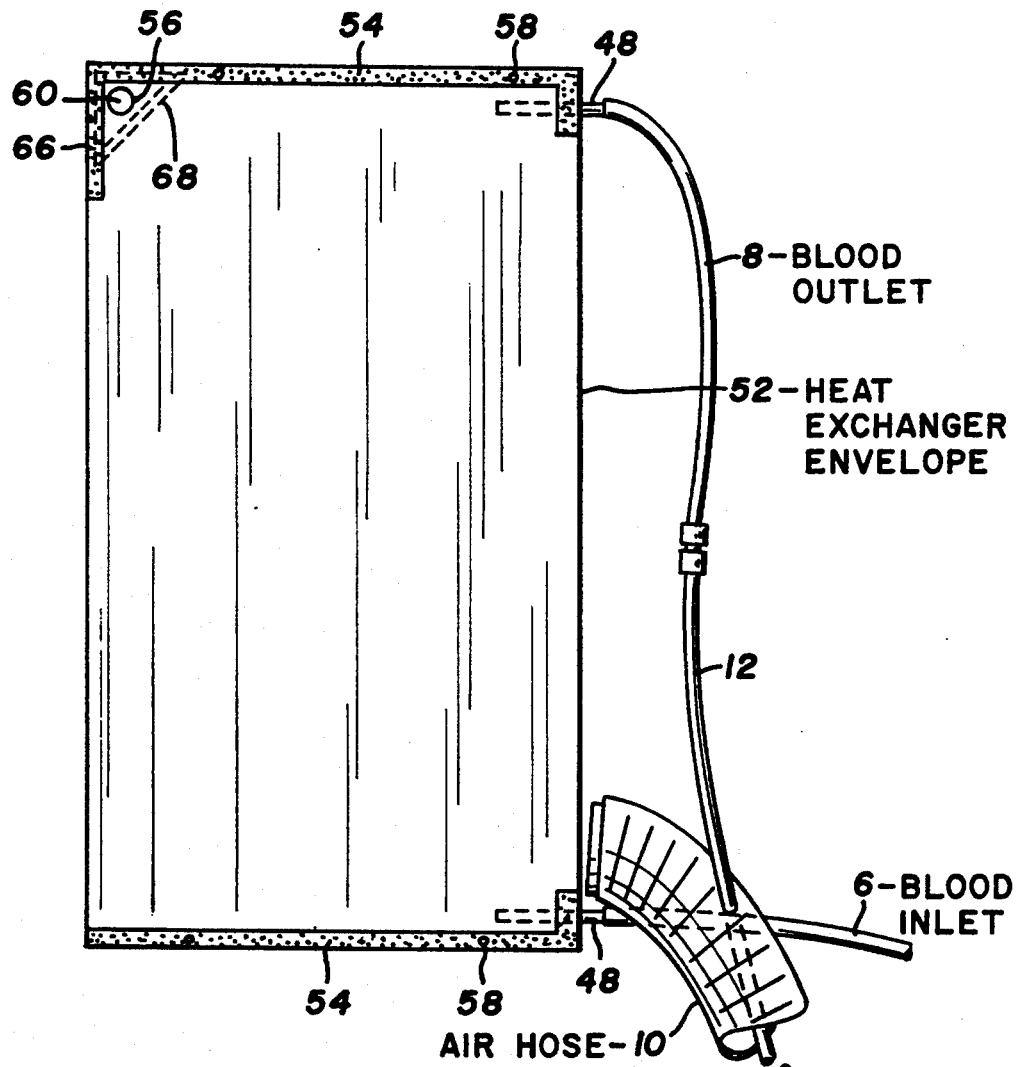
FIG. 5 is a similar front elevational view of the envelope showing a modified form of utilization of the air hose.
Figure 6:
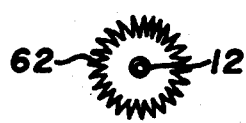
FIG. 6 is a transverse cross section on the line 6—6 of FIG. 5 and in the direction of the arrows.

FIGS. 5 and 6 illustrate the use of a fluted cylindrical paper filter 62 attached to the outlet end of warm air hose 10 to prevent particulate contamination of the operating room in which the blood warmer is being used.

Figure 9:
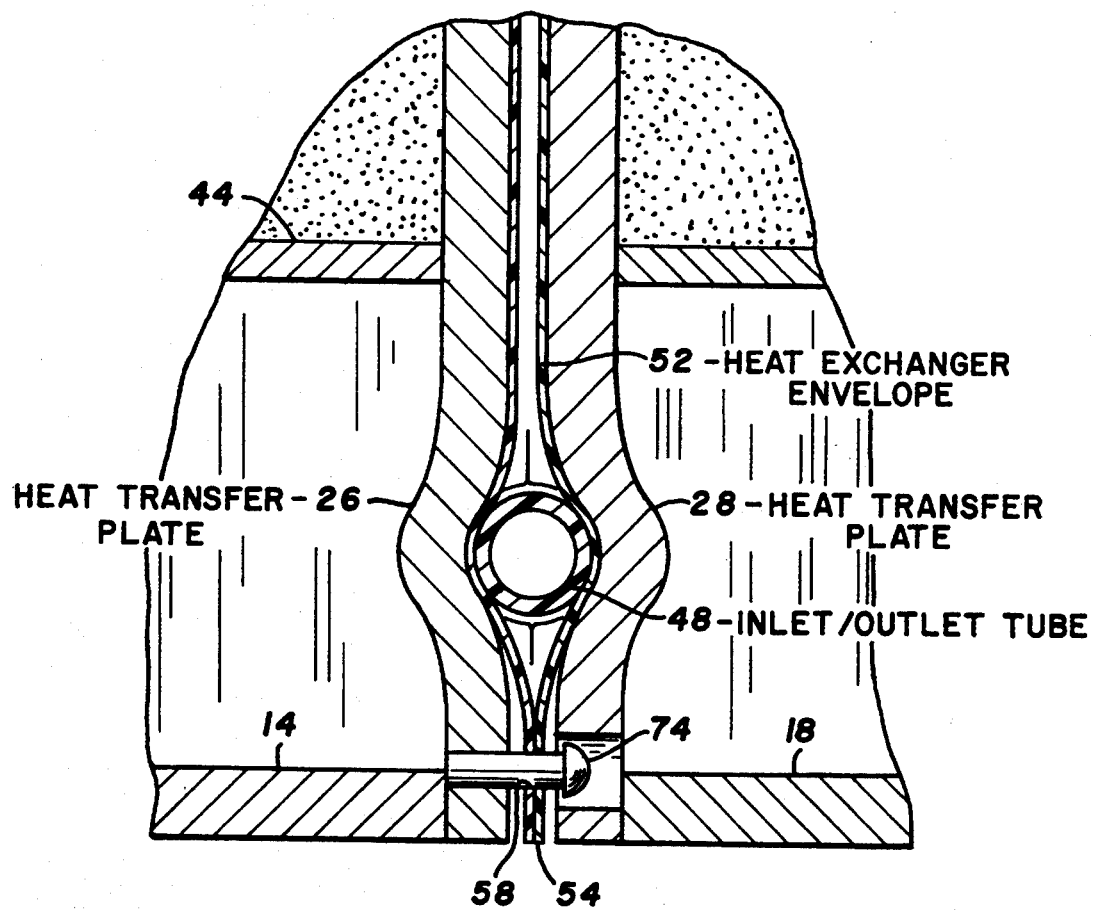
FIG. 9 is a fragmentary section on an enlarged scale on the line 9—9 of FIG. 2 and in the direction of the arrows.

In the operation of the system cold blood enters the heat exchanging envelope 52 through inlet tube 6 and is warmed as it flows through the envelope in a thin, flat ribbon 76 to the outlet tube 8, sandwiched between the heat transfer plates 26 and 28 as shown in FIG. 9. Simultaneously room air is drawn into the blood warmer housing unit 18 through filter/screen 32 by fan 34 and warmed by passage across heating fins 40 and 42 which are automatically maintained at physiologic temperature by the condensation heating unit 44. The warmed air is directed into insulated warm air hose 10 through which the intravenous line 12 to the patient also passes. The already warmed blood is thus surrounded by warm air as it traverses the intravenous flow line to the patient and is not cooled toward room temperature at low flow rates as it would be if exposed to convective cooling by ambient room air.

Although for convenience the system has been described with reference to warming of blood, it is to be understood that its use is equally applicable to other intravenous or irrigating fluids as are customarily administered to patients.

It is apparent that many modifications and variations of this invention as hereinbefore set forth may be made without departing from the spirit and scope thereof. The specific embodiments described are given by way of example only and the invention is limited only by the terms of the appended claims.

I claim:

1. A system for warming blood or other liquids to body temperature for infusion into a patient comprising:
   A) a blood warmer apparatus having a pair of closely spaced apart heat transfer plates each forming one face of a housing containing flat vapor condensation heating units therein, and adapted to receive a flat heat exchanging blood warming envelope held clamped between said closely spaced apart heat transfer plates,
   B) an air heating unit within one of said housings including:
      1) a cool air inlet to said housing,
      2) heat transfer fins on the wall of the vapor condensation heater unit opposite from the heat transfer plate,
      3) a fan and guides within the housing for conducting air from said inlet past said fins, and
      4) a warmed air outlet from said housing, and
   C) an external outer elongated air hose connected at one end to said warmed air outlet and extending to the patient, said air hose adapted to receive an inner elongated blood flow line therein.

2. A system according to claim 1 wherein said air hose is composed of insulating synthetic resinous plastic foam.

3. A system according to claim 2 wherein said air hose is composed of closed cell polyethylene foam.

4. A system according to claim 1 wherein a fluted cylindrical paper filter is disposed in the downstream end of the warm air hose.

5. A system for warming blood or other liquids to body temperature for infusion into a patient comprising:
   A) a blood warmer apparatus having a pair of closely spaced apart heat transfer plates each forming one face of a housing containing flat vapor condensation heating units therein,
   B) a flat disposable heat exchanging envelope held clamped between said closely spaced apart heat transfer plates, said envelope having a blood inlet adapted to be connected to a source of blood to be warmed and a warmed blood outlet adapted to be connected to a flow line to the patient,
   C) an air escape vent adjacent the topmost edge of said envelope and a hydrophobic filter covering said vent,
   D) an air heating unit within one of said housings including:
      1) a cool air inlet to said housing,
      2) heat transfer fins on the wall of the vapor condensation heater unit opposite from the heat transfer plate,
      3) a fan and guides for conducting air from said inlet past said fins, and
      4) a warmed air outlet from the housing,
   E) an external outer elongated air hose connected at one end to said warmed air outlet and extending to the patient, and
   F) an inner elongated blood flow line within said outer hose, one end of said inner flow line being connected to said warmed blood outlet and the opposite end extending to the patient.

6. A system according to claim 5 wherein:
   A) said heat exchanging envelope is composed of a flattened thin walled tube of synthetic resinous plastic material,
   B) a heat seal closure is provided at each end of said tube, forming the respective top and bottom edges of said envelope,
   C) said blood inlet and outlet tubes are sealed into said heat sealed edges of the envelope adjacent one side edge thereof,
   D) said air escape vent is disposed adjacent to the top side edge of the envelope opposite from the blood inlet/outlet tube, and
   E) a hydrophobic filter covering said vent.

7. A system according to claim 6 wherein said hydrophobic filter is a thin porous right triangular sheet disposed between the envelope side walls with edges heat sealed thereto along the top and side edges thereof, and heat sealed along the hypotenuse of the filter only to the envelope side wall having the vent.

8. A system according to claim 6 wherein the walls of said envelope adjacent to the blood inlet/outlet regions at the top and bottom end edges are heat sealed together in spaced apart spots defining interior flow channels.

9. A system according to claim 8 wherein said sealed spots are more closely spaced adjacent the inlet and outlet tubes.

10. A system according to claim 6 wherein said envelope is composed of about 4 mil flat-lay polyethylene tubing and said blood inlet and outlet tubes are composed of about ⅛ to ¼ inch inside diameter polyethylene tubing.

11. A system according to claim 5 wherein said air hose is composed of insulating synthetic resinous plastic foam.

12. A system according to claim 11 wherein said air hose is composed of closed cell polyethylene foam.

13. A system according to claim 5 wherein a fluted cylindrical paper filter is disposed in the downstream end of the warm air hose.

14. A flat disposable heat exchanging envelope for warming blood, said envelope being adapted to be clamped between closely spaced apart heat transfer plates of a blood warming apparatus and comprising:
   A) a flattened thin walled tube of synthetic resinous plastic material,
   B) a heat seal closure at each end of said tube, forming the respective top and bottom edges of said envelope,
   C) a blood inlet/outlet tube heat sealed into each of said respective top and bottom edges of the envelope adjacent one side edge thereof,
   D) an air escape vent in one side wall of the envelope adjacent the top edge thereof, and
   E) a hydrophobic filter covering said vent.

15. A blood warming envelope according to claim 14 wherein:
   A) said air escape vent is disposed adjacent the top side edge of the envelope opposite from the blood inlet/outlet tube, and B) said hydrophobic filter is a thin porous right triangular sheet disposed between the envelope side walls with edges heat sealed thereto along the top and side edges thereof, and heat sealed along the hypotenuse of the filter only to the envelope side wall having the vent.

16. A blood warming envelope according to claim 14 wherein the side walls of said envelope adjacent to the blood inlet/outlet regions at the top and bottom end edges are heat sealed together in spaced apart spots defining interior flow channels.

17. A blood warming envelope according to claim 16 wherein said sealed spots are more closely spaced adjacent the inlet and outlet tubes.

18. A blood warming envelope according to claim 14 wherein said envelope is composed of about 4 mil flat-lay polyethylene tubing and said blood inlet and outlet are composed of about $\frac{1}{8}$ to $\frac{1}{4}$ inch inside diameter polyethylene tubing.

19. A blood warming envelope according to claim 14 wherein:
   A) an elongated insulating air hose is provided, and
   B) a blood flow line connected to the outlet tube of said envelope, penetrates the wall of said air hose adjacent one end, and extends within said hose to the opposite end.

* * * * *